(12) United States Patent
Cerundolo

(10) Patent No.: US 7,569,059 B2
(45) Date of Patent: Aug. 4, 2009

(54) METHOD AND APPARATUS FOR SURGICAL REPAIR

(75) Inventor: Daniel Cerundolo, Hingham, MA (US)

(73) Assignee: Arthroscopic Innovations LLC, Weymouth, MA (US)

( * ) Notice: Subject to any disclaimer, the term of this patent is extended or adjusted under 35 U.S.C. 154(b) by 75 days.

(21) Appl. No.: 11/110,540

(22) Filed: Apr. 20, 2005

(65) Prior Publication Data
US 2006/0241619 A1    Oct. 26, 2006

(51) Int. Cl.
*A61F 5/00* (2006.01)
(52) U.S. Cl. ................ 606/86 R; 623/11.11; 623/13.11
(58) Field of Classification Search ............... 606/86, 606/96, 98, 104, 148–150, 86 R, 62–67; 623/11.11, 623/13.11–13.19
See application file for complete search history.

(56) References Cited

U.S. PATENT DOCUMENTS

| | | | |
|---|---|---|---|
| 3,976,079 A | 8/1976 | Samuels et al. | |
| 4,103,683 A | 8/1978 | Neufeld | |
| 4,257,411 A | * 3/1981 | Cho | ............................ 606/96 |
| 4,535,768 A | 8/1985 | Hourahane et al. | |
| 4,633,869 A | 1/1987 | Schmieding | |
| 4,672,957 A | 6/1987 | Hourahane | |
| 4,722,331 A | 2/1988 | Fox | |
| 4,739,751 A | 4/1988 | Sapega et al. | |
| 4,781,182 A | 11/1988 | Purnell et al. | |
| 4,920,958 A | 5/1990 | Walt et al. | |
| 4,945,904 A | 8/1990 | Bolton et al. | |
| 5,042,983 A | 8/1991 | Rayhack | |
| 5,112,337 A | 5/1992 | Paulos et al. | |
| 5,163,940 A | 11/1992 | Bourque | |
| 5,178,621 A | 1/1993 | Cook et al. | |
| 5,211,647 A | 5/1993 | Schmieding | |
| 5,217,471 A | 6/1993 | Burkhart | |
| 5,222,962 A | 6/1993 | Burkhart | |

(Continued)

FOREIGN PATENT DOCUMENTS

| | | |
|---|---|---|
| EP | 0 824 893 A1 | 2/1998 |
| WO | WO 01/97677 A2 | 12/2001 |
| WO | WO 03/007799 A2 | 1/2003 |

OTHER PUBLICATIONS

Arthrex, Shoulder Arthroscopy & Mini-Open Repairs, TissueButton™, printed from www.arthrex.com, 2005.

(Continued)

*Primary Examiner*—Eduardo C Robert
*Assistant Examiner*—Tara R George
(74) *Attorney, Agent, or Firm*—Wolf, Greenfield & Sacks, P.C.

(57) ABSTRACT

A method and apparatus for performing a surgical repair may involve the use of a guide to form a passageway through the body portion, such as bone. In addition, or alternately, the guide may be used to provide a suture or suture-like material through a passageway, e.g., to secure to a material relative to the body portion. The passageway may be formed by first and second intersecting holes formed in the body portion. Both ends of a suture may be positioned in the passageway, and be secured relative to the body portion near one of the openings into the passageway. A straightened pathway between the first and second openings of the passageway may be formed, e.g., using a flossing operation.

26 Claims, 5 Drawing Sheets

U.S. PATENT DOCUMENTS

| | | | |
|---|---|---|---|
| 5,234,434 | A | 8/1993 | Goble et al. |
| 5,250,055 | A * | 10/1993 | Moore et al. ............... 606/148 |
| 5,269,786 | A | 12/1993 | Morgan |
| 5,320,626 | A | 6/1994 | Schmieding |
| 5,330,468 | A | 7/1994 | Burkhart |
| 5,334,205 | A | 8/1994 | Cain |
| 5,350,383 | A | 9/1994 | Schmieding et al. |
| 5,368,596 | A | 11/1994 | Burkhart |
| 5,403,321 | A | 4/1995 | DiMarco |
| 5,425,733 | A | 6/1995 | Schmieding |
| 5,431,651 | A | 7/1995 | Goble |
| 5,466,243 | A | 11/1995 | Schmieding et al. |
| 5,575,801 | A | 11/1996 | Habermeyer et al. |
| 5,601,562 | A | 2/1997 | Wolf et al. |
| 5,603,716 | A | 2/1997 | Morgan et al. |
| 5,620,449 | A | 4/1997 | Faccioli et al. |
| 5,626,613 | A | 5/1997 | Schmieding |
| 5,643,320 | A * | 7/1997 | Lower et al. ............... 606/232 |
| 5,681,333 | A * | 10/1997 | Burkhart et al. ............ 606/148 |
| 5,683,401 | A | 11/1997 | Schmieding et al. |
| 5,690,677 | A | 11/1997 | Schmieding et al. |
| 5,743,916 | A | 4/1998 | Greenberg et al. |
| 5,746,752 | A | 5/1998 | Burkhart |
| 5,766,179 | A | 6/1998 | Faccioli et al. |
| 5,833,691 | A | 11/1998 | Bimman |
| RE36,020 | E | 12/1998 | Moore et al. |
| 5,918,604 | A * | 7/1999 | Whelan ..................... 128/898 |
| 5,919,196 | A | 7/1999 | Bobic et al. |
| 5,951,559 | A | 9/1999 | Burkhart |
| 5,964,783 | A | 10/1999 | Grafton et al. |
| 5,993,451 | A | 11/1999 | Burkhart |
| 6,027,523 | A | 2/2000 | Schmieding |
| 6,039,742 | A | 3/2000 | Krettek et al. |
| 6,074,403 | A | 6/2000 | Nord |
| 6,113,604 | A | 9/2000 | Whittaker et al. |
| 6,117,162 | A | 9/2000 | Schmieding et al. |
| 6,120,511 | A | 9/2000 | Chan |
| 6,132,433 | A | 10/2000 | Whelan |
| 6,214,031 | B1 | 4/2001 | Schmieding et al. |
| 6,221,084 | B1 * | 4/2001 | Fleenor ..................... 606/148 |
| 6,267,766 | B1 | 7/2001 | Burkhart |
| 6,270,503 | B1 | 8/2001 | Schmieding |
| 6,319,270 | B1 | 11/2001 | Grafton et al. |
| 6,371,124 | B1 | 4/2002 | Whelan |
| 6,387,129 | B2 | 5/2002 | Rieser et al. |
| 6,416,518 | B1 | 7/2002 | DeMayo |
| 6,461,373 | B2 | 10/2002 | Wyman et al. |
| 6,511,499 | B2 | 1/2003 | Schmieding et al. |
| 6,517,552 | B1 | 2/2003 | Nord et al. |
| 6,517,564 | B1 | 2/2003 | Grafton et al. |
| 6,524,317 | B1 | 2/2003 | Ritchart et al. |
| 6,537,319 | B2 | 3/2003 | Whelan |
| 6,540,750 | B2 | 4/2003 | Burkhart |
| 6,544,281 | B2 | 4/2003 | ElAttrache et al. |
| 6,575,976 | B2 | 6/2003 | Grafton |
| 6,592,588 | B1 | 7/2003 | Bobic et al. |
| 6,610,064 | B1 * | 8/2003 | Goble et al. ............... 606/72 |
| 6,616,665 | B2 | 9/2003 | Grafton et al. |
| 6,616,674 | B2 | 9/2003 | Schmieding |
| 6,623,524 | B2 | 9/2003 | Schmieding |
| 6,629,977 | B1 | 10/2003 | Wolf |
| 6,641,597 | B2 | 11/2003 | Burkhart et al. |
| 6,652,563 | B2 | 11/2003 | Dreyfuss |
| 6,663,656 | B2 | 12/2003 | Schmieding et al. |
| 6,716,234 | B2 | 4/2004 | Grafton et al. |
| 6,733,529 | B2 | 5/2004 | Whelan |
| 7,032,599 | B2 * | 4/2006 | May et al. ............... 128/898 |
| 7,207,995 | B1 * | 4/2007 | Vandewalle ............... 606/104 |
| 2001/0037119 | A1 | 11/2001 | Schmieding |
| 2001/0037131 | A1 | 11/2001 | Schmieding et al. |
| 2001/0051807 | A1 | 12/2001 | Grafton |
| 2002/0013608 | A1 | 1/2002 | ElAttrache et al. |
| 2002/0022862 | A1 | 2/2002 | Grafton et al. |
| 2002/0032466 | A1 | 3/2002 | Grafton et al. |
| 2002/0120275 | A1 | 8/2002 | Schmieding et al. |
| 2002/0133165 | A1 | 9/2002 | Whittaker et al. |
| 2002/0143364 | A1 | 10/2002 | Burkhart |
| 2003/0004545 | A1 | 1/2003 | Burkhart et al. |
| 2003/0050666 | A1 | 3/2003 | Grafton |
| 2004/0092936 | A1 * | 5/2004 | Miller et al. ............... 606/72 |
| 2004/0093031 | A1 | 5/2004 | Burkhart et al. |
| 2004/0106950 | A1 | 6/2004 | Grafton et al. |
| 2004/0172062 | A1 | 9/2004 | Burkhart |
| 2004/0193172 | A1 | 9/2004 | Ross et al. |
| 2004/0199166 | A1 | 10/2004 | Schmieding et al. |
| 2005/0038437 | A1 | 2/2005 | McDevitt et al. |

OTHER PUBLICATIONS

ArthroCare Corporation, Atlantech® Collection, ACL Reconstruction Instrumentation, Bilok® ACL Reconstruction Interference Screws, Suture Anchors, Handheld Instruments, Shoulder Retractor, CAPS-LOCK™ Shoulder Cannulal, Chondra Pick Instruments, www.arthrocare.com/sports_medicine/sm_phy_products_atlantech.htm, Jan. 5, 2005, © 2004 ArthroCare Corporation.

Bio-Phase™ II Suture Anchor, © 2003 Arthrotek, Inc., www.arthrotek.com/products/anchors_biophaseii.cfm.

Brochure: Closing the Gap in Soft Tissue Repair, The AutoCuff System, Opus Medical, Inc., 2004, A 1006-0504.

Burkhart et al., Arthroscopic Rotator Cuff Repair: Analysis of Results by Tear Size and by repair Technique—Margin Convergence Versus Direct Tendon-To-Bone Repair, 2001, Journal of Arthroscopic and Related Surgery, vol. 17, No. 9 (Nov.-Dec. 2001), pp. 905-912.

Burkhart et al., Arthroscopic Subscapularis Tendon Repair: Technique and Preliminary Results, 2002, Journal of Arthroscopic and Related Surgery, vol. 18, No. 5 (May-Jun.), pp. 454-463.

Burkhart et al., Clinical and Anatomic Considerations in the Use of a New Anterior Inferior Subaxillary Nerve Arthroscopy Portal, 1996, Journal of Arthroscopic and Related Surgery, vol. 12, No. 5, (Oct.), pp. 634-637.

Burkhart et al., Shoulder Arthroscopy New Concepts, 1996, Arthroscopic Surgery, Part 1 (Clinics in Sports Medicine) vol. 15, No. 4 (Oct.), pp. 635-653.

Burkhart et al., Slap Lesions in the Overhead Athlete, 2001, Orthopedic Clinics of North America, Vo. 32, No. 3, (Jul. 2001).

Burkhart, A Stepwise Approach to Arthroscopic Rotator Cuff Repair Based on Biomechanical Principles, 2000, Journal of Arthroscopic and Related Surgery, vol. 16, No. 1, pp. 82.90.

Burkhart, Arthroscopic Treatment of Massive Rotator Cuff Tears, Sep. 2001, Clinical Orthopaedics and Related Research Vol. 1, (390), pp. 107-118.

Burkhart, Biomechanics of Rotator Cuff Repair: Converting the Ritual to a Science, AAOS Instructional Course Lectures, vol. 47, pp. 43-50, 1998.

Burkhart, Partial Repair of Massive Rotator Cuff Tears: The evolution of a Concept, 1997, The Rotator Cuff, Part 1 (Orthopedic Clinics of North America), vol. 28, No. 1, pp. 125-132.

Burkhart, Shoulder Scope: Corkscrew Rotator Cuff Repair, Arthroscopic Knot Tying, www.shoulder.com, San Diego Shoulder Arthroscopy Inc., 1997.

Burkhart, Shoulder Scope: Corkscrew Rotator Cuff Repair, Corkscrew Insertion, www.shoulder.com, San Diego Shoulder Arthroscopy Inc., 1997.

Burkhart, Shoulder Scope: Corkscrew Rotator Cuff Repair, Dual Corkscrew and Matress Suture Technique (1 of 2), www.shoulder.com, San Diego Shoulder Arthroscopy Inc., 1997.

Burkhart, Shoulder Scope: Corkscrew Rotator Cuff Repair, Dual Corkscrew and Matress Suture Technique (2 of 2), www.shoulder.com, San Diego Shoulder Arthroscopy Inc., 1997.

Burkhart, Shoulder Scope: Corkscrew Rotator Cuff Repair, Knot Completion, www.shoulder.com, San Diego Shoulder Arthroscopy Inc., 1997.

Burkhart, Shoulder Scope: Corkscrew Rotator Cuff Repair, Mini-Open Incision, www.shoulder.com, San Diego Shoulder Arthroscopy Inc., 1997.
Burkhart, Shoulder Scope: Corkscrew Rotator Cuff Repair, Patient Positioning, www.shoulder.com, San Diego Shoulder Arthroscopy Inc., 1997.
Burkhart, Shoulder Scope: Corkscrew Rotator Cuff Repair, Portal Placement, www.shoulder.com, San Diego Shoulder Arthroscopy Inc., 1997.
Burkhart, Shoulder Scope: Corkscrew Rotator Cuff Repair, Rotator Cuff Mobilization www.shoulder.com, San Diego Shoulder Arthroscopy Inc., 1997.
Burkhart, Shoulder Scope: Corkscrew Rotator Cuff Repair, Suture Placement and Knot Tying, www.shoulder.com, San Diego Shoulder Arthroscopy Inc., 1997.
Burkhart, Shoulder Scope: Corkscrew Rotator Cuff Repair, Suture Retrieval, www.shoulder.com, San Diego Shoulder Arthroscopy Inc., 1997.
Burkhart, Shoulder Scope: Corkscrew Rotator Cuff Repair, Trough Preparation, www.shoulder.com, San Diego Shoulder Arthroscopy Inc., 1997.
Burkhart, Shoulder Scope: Corkscrew Rotator Cuff Repair, Vertical Switch Preparation, www.shoulder.com, San Diego Shoulder Arthroscopy Inc., 1997.
Burkhart, Tissue Fixation Security in Transosseous Rotator Cuff Repairs: A Mechanical Comparison of Simple Versus Mattress Sutures, 1996, Journal of Arthroscopic and Related Surgery, vol. 12, No. 6, (Dec.), pp. 704-708.
Cole et al., Anthroscopic Treatment of Anterior Glenohumeral Instability: Indications and Techniques, AAOS Instructional Course Lectures, vol. 53, pp. 545-558 (2004).
CurvTek website information re: Arthrotek CurvTek Bone Tunneling System, Jan. 7, 2005.
Gartsman, Arthroscopic Rotator Cuff Repair, Area Spalla, Arthroscopic, vol. III, N1, 2002, pp. 18-25.
Hawkins et al., The AutoCuff System for Rotator Cuff Repair (Surgical Technique), Opus Medical, Inc., 2004, A1022-06/04.
Higgins et al., Acromioclavicular Separation, Anatomical Chart Co., 1988.
http://home.flash.net/~rustyj/RCR.gif Anatomy of the Rotator Cuff, Rotator Cuff Repair, Jan. 5, 2005.
Johnson &Johnson, DePuy Mitek, Inc., Launches SPIRALOK™, the Latest Innovation in Minimally Invasive Rotator Cuff Repair, www.jnj.com/news/jnj_news/20040310_110538.htm, 2004.
Kessler, et al., Arthrotek, Inc., RCB™ Rotator Cuff Buttress © 2003 Arthrotek, Inc.
Linvatec Corporation, Mini-Open Rotator Cuff Repair System, Shutt® Suture Punch System, Tissue Repair Systems, Spectrum® Tissue Repair System www.Linvatec.com 2004.
Lo et al., Arthroscopic Coracoplasty Through the Rotator Interval, 2003, Journal of Arthroscopic and Related Surgery, vol. 19, No. 6 (Jul.-Aug.), pp. 667-671.
Lo et al., Arthroscopic Repair of Massive, Contracted Immobile Rotator Cuff Tears Using Single and Double Interval Slides: Technique and Preliminary Results, 2004, Journal of Arthroscopic and Related Surgery, vol. 20, No. 1 (Jan.), pp. 22-33.
Lo et al., Combined Subcoracoid and Subacromial Impingement in Association with Anterosuperior Rotator Cuff Tears: An Arthroscopic Approach, 2003, Journal of Arthroscopic and Related Surgery, vol. 19, No. 10 (Dec.), pp. 1068-1078.
Lo et al., Current Concepts in Arthroscopic Rotator Cuff Repair, 2003, American Journal of Sports Medicine, vol. 31, No. 2, pp. 308-324.
Lo et al., Double-Row Arthroscopic Rotator Cuff Repair: Re-Establishing the Footprint of the Rotator Cuff, 2003, Journal of Arthroscopic and Related Surgery, Vo. 19, No. 9 (Nov.), pp. 1035-1042.
Lo et al., The Interval Slide in Continuity: A Method of Mobilizing the Anterosuperior Rotator Cuff Without Disrupting the Tear Margins, 2004, Journal of Arthroscopic and Related Surgery, vol. 20, No. 4 (Apr.) pp. 435-441.
Lo et al., Triple Labral Lesions: Pathology and Surgical Repair Technique—Report of Seven Cases, 2005, Journal of Arthroscopic and Related Surgery, vol. 21, No. 2, (Feb.) pp. 186-193.
Opus Medical: Technology, www.opusmedical.com/technology.htm, Advanced Technology For Totally Arthroscopic Rotator Cuff Repair, Jan. 5, 2005, pp. 1-3.
Richards et al., Arthroscopic Humeral Avulsion of the Glenohumeral Ligaments (HAGL) Repair, Journal of Arthroscopic and Related Surgery, 2004, vol. 20, No. 6, pp. 134-141.
Richards et al., Arthroscopic-Assisted Biceps Tenodesis for Rupture of the Long Head of Biceps Brachii: The Cobra Procedure, 2004, Journal of Arthroscopic and Related Surgery, vol. 20, No. 6 (Jul.-Aug.), pp. 201-207.
Richards et al., Margin Convergence of the Posterior Rotator Cuff to the Biceps Tendon, 2004, Journal of Arthroscopic and Related Surgery, vol. 20, No. 7, (Sep.), pp. 771-775.
Richards et al., Subscapurlaris Tears: Arthroscopic Repair Techniques, 2003, Orthop. Clin. N. Am. vol. 34, pp. 485-498.
Rotator Cuff Repair, www.shands.org/health/information/article/007207.htm, 2003.
Ryu et al., Complex Topics in Arthroscopic Subacromial Space and Rotator Cuff Surgery, 2002, Journal of Arthroscopic and Related Surgery, vol. 18, No. 2 (Feb., Suppl. 1), pp. 51-64.
Shoulder Solutions—Shoulder Anatomy—Shoulder Bones, www.shouldersolutions.com/anatomy_2.php Jan. 5, 2005.
Shoulder Solutions—Shoulder Anatomy—Shoulder Muscles and Tendons, www.shouldersolutions.com, Jan. 5, 2005.
Smith&Nephew, RotorloC Absorbable Rotator Cuff Suture Anchor, Smith and Nephew Endoscopy, http://endo.smith-nephew.com, Jan. 5, 2005.
Smith&Newphew, Cannula Line, Aug. 17, 2004 www.smith-newphew.com.
Surgical Solutions, Inc. ExpressSew Suture Passer, Suture Passing System, The 5mm solution for tissue repair, © 2004 Surgical Solutions, Inc.
University of Washington Orthopaedics & Sports Medicine, Surgery for Rotator Cuff Tears, Rotator cuff tears of the shoulder, www.orthop.washington.edu/faculty/Matsen/rotatorcuffsurgery/05, Edited by Frederick A. Matsen III, M.D., pp. 1-4, 2003.
University of Washington Orthopaedics & Sports Medicine, Surgery for Rotator Cuff Tears, About rotator cuff surgery, www.orthop.washington.edu/faculty/Matsen/rotatorcuffsurgery/05, Edited by Frederick A. Matsen III, M.D., pp. 1-2, 2003.
University of Washington Orthopaedics & Sports Medicine, Surgery for Rotator Cuff Tears, About surgery for rotator cuff tears, www.orthop. washington.edu/faculty/Matsen/rotatorcuffsurgery/05, Edited by Frederick A. Matsen III, M.D., pp. 1-2, 2003.
Uribe, Closing the Gap in Arthroscopic Rotator Cuff Repair: A Review of Our Experience with 40 Cases Using the AutoCuff System, Opus Medical, Inc., 2004, A1021-03/04.
Worland, et al., Arthrotek, Rotator Cuff Repair, RC Needle, www.arthrotek.com © 2000, Arthrotek, Inc.
International Search Report and Written Opinion for International Application No. PCT/US2006/013617 dated Oct. 23, 2006.
Notice of Allowance, U.S. Appl. No. 11/110,004, mailed Aug. 10, 2007.

* cited by examiner

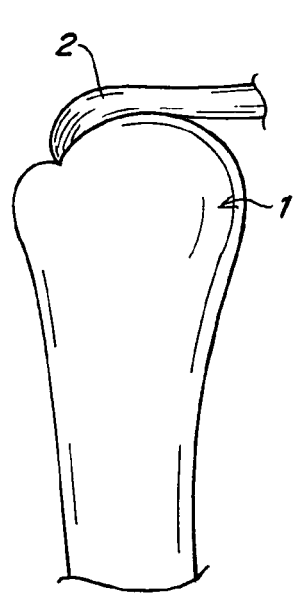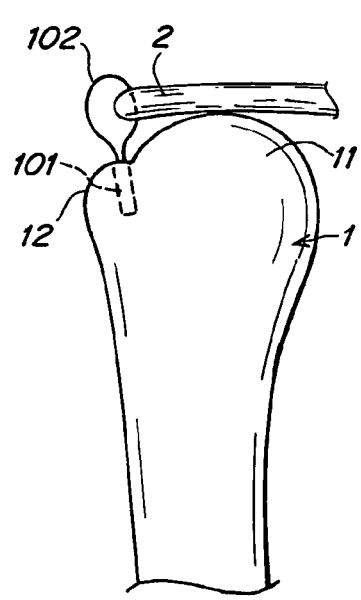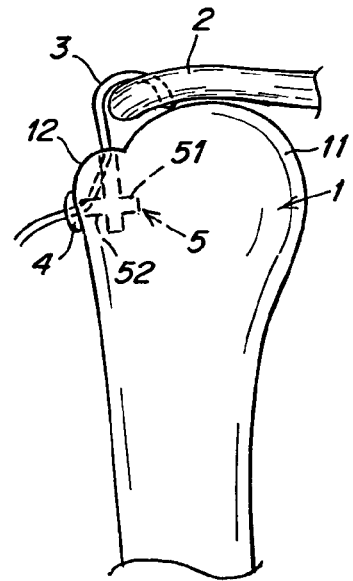
Fig. 1    Fig. 2    Fig. 3
         PRIOR ART
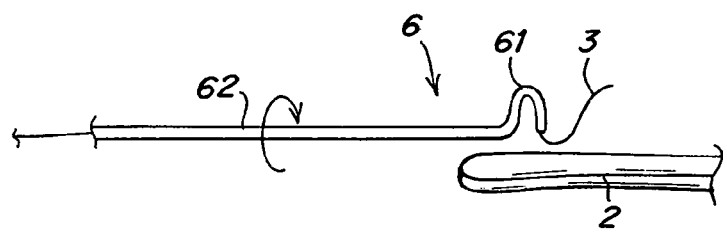
Fig. 4
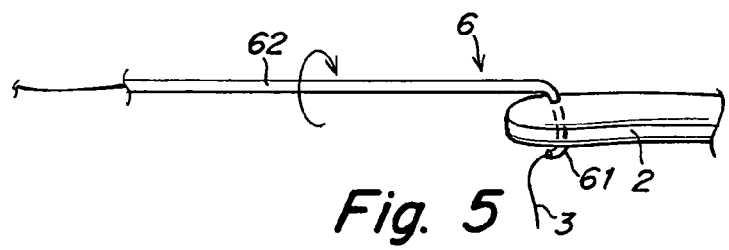
Fig. 5
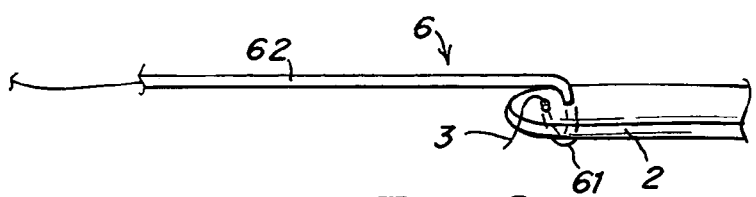
Fig. 6

METHOD AND APPARATUS FOR SURGICAL REPAIR

BACKGROUND OF INVENTION

1. Field of Invention

This invention relates to methods and apparatus for surgical repair.

2. Discussion of Related Art

Suture anchors and other suture fixation devices are often used for surgical repair, such as when attempting to secure one body portion relative to another or relative to a surgical implant or other device. For example, tendon damage frequently requires surgery for repair, e.g., to reattach a torn or separated tendon to the bone to which the tendon would normally be attached. Shoulder rotator cuff injuries typically involve damage to the rotator cuff tendon such that the tendon, or at least a portion thereof, requires reattachment to the humerus. FIG. 1 shows a schematic diagram of a humerus 1 and a portion of a rotator cuff tendon 2 that is normally attached to the head of the humerus. In one type of damage to the rotator cuff, the tendon 2 may detach or be partially torn from the humerus 1, such as that shown schematically in FIG. 2. Such damage may be repaired by reattaching the rotator cuff tendon to the humerus 1 by a suture or other fixation so that the body's normal healing processes can naturally effect reattachment of the tendon to the bone. One repair technique for reattaching the rotator cuff 2 to the humerus 1 involves fixing an anchor 101 at a margin between the articulating portion 11 of the humerus 1 and the humerus' greater tuberosity 12. A suture 102 is secured to the rotator cuff 2 and the anchor 101, and the suture 102 is tensioned so that the rotator cuff 2 is held in place close to the humerus 1. Thereafter, the body may reestablish the proper attachment of the rotator cuff 2 to the humerus 1.

SUMMARY OF INVENTION

In one aspect of the invention, a rotator cuff repair technique is provided that does not necessarily require placement of an anchor at a margin between the articulating surface and the greater tuberosity of the humerus. In one embodiment, an anchor or other suture fixation device, if provided, may be positioned at a lateral side of the humerus, away from the rotator cuff/humerus attachment point.

Other aspects of the invention are provided that are not necessarily restricted to use in rotator cuff repair. For example, in one aspect of the invention, a passageway may be formed through a body portion by forming first and second intersecting holes in the body portion. A tissue, prosthetic or other material may be secured relative to the body portion using a suture that passes through the passageway formed by the intersecting holes. In one aspect of the invention, a suture may be passed through the passageway using a guide member, such as a perforator guide, located at least partially in the passageway.

In one aspect of the invention, a method for performing a surgical repair includes providing a first hole in a body portion, positioning a guide relative to the first hole, and forming a second hole using the guide to define a location of the second hole so that the second hole intersects with the first hole and forms a passageway through the body portion. The guide may be used to provide a suture or suture-like material through the passageway, and a repair suture may be secured to a material to be secured relative to the body portion. At least a portion of the repair suture may be positioned in the passageway, and the material secured relative to the body portion using the repair suture.

In another aspect of the invention, a method for forming a passageway in bone includes providing a first hole into bone of a humerus, and securing a first guide member relative to the first hole. The first guide member may be positioned with respect to a reference structure, and a second hole may be formed in the bone using the reference structure to define the location of the second hole relative to the first hole. The second hole may be formed so as to intersect the first hole and form a passageway through the bone. At least a portion of a suture may be passed through the passageway, and a rotator cuff tendon may be secured relative to the bone using the suture.

In another aspect of the invention, a method includes forming a passageway through a body portion, where the passageway is formed by first and second intersecting holes formed in the body portion. First and second guide tubes may be secured, respectively, relative to the first and second holes, and a suture or suture-like material may be provided into the first guide tube. The suture or suture-like material may be retrieved from the second guide tube.

In another aspect of the invention, a method includes forming a passageway through a body portion, where the passageway extends from a first opening near a material to be secured relative to the body portion to a second opening positioned away from the material. A suture may be secured to the material, where the suture has two ends extending from the material. The two ends of the suture may be positioned in the passageway, and the two ends of the suture may be secured relative to the body portion near the second opening.

In another aspect of the invention, a method includes forming a passageway through a body portion, where the passageway extends from a first opening to a second opening. An elongated element may be manipulated in the passageway to form a straightened pathway between the first and second openings. A suture may be secured to a material, such as a tissue, prosthetic and/or other, and at least a portion of the suture may be positioned in the passageway. The suture may be secured relative to the body portion, e.g., to secure the material relative to the body portion.

BRIEF DESCRIPTION OF DRAWINGS

Various aspects of the invention are described with reference to illustrative embodiments, wherein like numerals reference like elements, and wherein:

FIG. 1 is a schematic diagram of a head of a humerus and attached rotator cuff tendon;

FIG. 2 shows a prior art technique for repairing a rotator cuff injury;

FIG. 3 is a schematic diagram of a tissue repair arrangement in accordance with an aspect of the invention;

FIGS. 4-6 show the use of a needle for placing a suture in a tissue in accordance with the invention;

DETAILED DESCRIPTION

Figure 7:
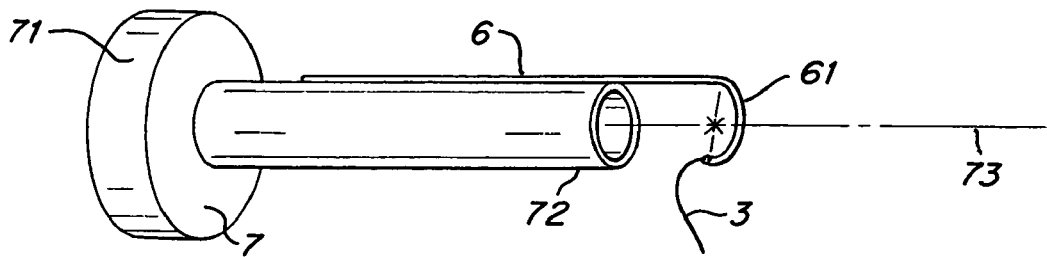
FIG. 7 shows a needle in engagement with a cannula in accordance with an aspect of the invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. Also, the term "guide" or "guiding" as used herein means actually guiding an element in its movement, and/or providing some reference for the location of an element. For example, "guiding" the formation of a hole in a body portion may mean guiding a bone perforator when actually forming the hole and/or providing a starting location for the hole formation.

Various aspects of the invention are described below with reference to specific embodiments. For example, aspects of the invention are described in the context of performing a rotator cuff repair. However, it should be understood that aspects of the invention are not necessarily restricted to rotator cuff repair techniques, or even to surgical techniques performed on a shoulder. Rather, various aspects of the invention may be used in any suitable surgical procedure. In addition, various aspects of the invention may be used alone, and/or in combination with any other aspects of the invention.

In one aspect of the invention, a method for performing a surgical procedure may include providing a passageway in a body portion where the passageway extends from a first opening in the body portion, e.g., a bone, to a second opening in the body portion. A suture may be placed in or otherwise secured to a material, e.g., a tissue, prosthetic, surgical implant, etc., to be secured relative to the body portion and two ends of the suture extending away from the material may be positioned in the first opening and extend into the passageway. The material may be secured relative to the body portion by securing the two ends of the suture in the passageway relative to the body portion near the second opening. For example, a rotator cuff tendon may be secured to a humerus by a suture that is placed in the tendon and has two ends that extend through a passageway in the humerus having one opening near the rotator cuff and a second opening positioned away from the rotator cuff, such as at a lateral side of the humerus. The two ends of the suture may be positioned in the passageway and secured at or near the second opening at the lateral side of the humerus. In one embodiment, a suture fixation device may be positioned near the second opening to help secure the two suture ends.

In one aspect of the invention, a suture fixation device used to help secure a suture relative to a passageway in bone may be arranged so as to secure the suture relative to the bone at an opening into the bone by having a portion of the suture fixation device positioned outside of and adjacent the opening in contact with portions of cortical bone. By securing the suture (and potentially a tissue or other material engaged with the suture) relative to the bone by contact of the suture fixation device with cortical bone, the suture may be more securely fixed as compared to devices that engage with softer cancellous bone.

In another aspect of the invention, a suture fixation device may include a body having an inner end and an outer end and a pathway extending between the inner and outer ends. The inner end may be arranged to be positioned in a hole in a body portion, such as bone. The body may include a restriction in the pathway that relatively freely permits movement of a suture through the pathway in a first direction and inhibits movement of the suture through the pathway in a second direction opposite the first direction. Such a feature may help maintain tension on the suture, e.g., while a knot is being formed in the suture.

In another aspect of the invention, a passageway formed through a body portion, such as bone, may be made by first and second intersecting holes. That is, the first and second holes may be formed into the body portion so each originate at different starting points and intersect within the body portion. The holes may be formed at an angle to each other or may be colinear. A guide may be used to define the location of the first and/or second hole, e.g., may be used to guide the movement of a bone perforator when forming the first and/or second holes, and/or may be used to locate a starting point for the formation of the first or second holes. In addition, or alternately, the guide may be used to pass a suture through the passageway. For example, a portion of the guide may be secured relative to one or both of the holes and a suture or other material may be passed through the guide portion when passing the suture or other material through the passageway.

In one aspect of the invention, a guide apparatus may be used to form one or two holes used to form a passageway in a body portion and/or to pass a suture or other material through the passageway. For example, a first guide member may be secured relative to a first hole formed in bone. A second guide member may be arranged so that its orientation relative to the first guide member is known. The second guide member may be used to guide the identification of a starting point for the formation of the second hole and/or guide the movement of a bone perforator to form a second hole into the bone so that the orientation of the second hole is arranged in a known way relative to the first hole. Alternately, the second guide member may be secured relative to a second hole that intersects with the first hole. The first and second guide members may be positioned relative to each other, e.g., using a reference structure, so that distal ends of the guide members are positioned adjacent each other in the passageway. Suture or other material may be introduced into one of the guide members and fed to a point adjacent the other guide member. The suture or other material may be retrieved from the guide member, for example, by a hook-shaped member, grasper or other suture retriever.

In another aspect of the invention, a passageway formed by two intersecting holes, for example, and without limitation, at a 90 degree angle, such that the passageway is generally not straight may be altered so as to form a straightened pathway. For example, the two intersecting holes may respectively originate from first and second openings at separated locations on a body portion, such as bone. A suture or suture-like material may be passed through the passageway and manipulated so as to form a more straight pathway between the first and second openings. In one embodiment, the suture or suture-like material (e.g., a wire) may be tensioned and moved so as to cut and/or crush cancellous bone between the first and second openings. This may provide a straightened pathway for suture in the passageway.

Various aspects of the invention may be used in an open surgical procedure or in a closed procedure, such as an arthroscopic procedure. For example, a guide apparatus may be used in an open or closed procedure as an aid in forming a passageway through a body portion, for passing a suture or other material through a passageway, or for both forming a passageway and passing a suture or other material through the passageway. In a closed procedure, each guide member in the apparatus may be passed through respective portals. Portions of the guide apparatus may remain outside of the body, however, such as the reference structure. Also, various aspects of the invention may be used in any suitable surgical or other procedure involving any suitable body portions, such as bone, muscle, skin, vascular structures, digestive structures or other tissue, implants, mesh, or other medical devices, etc.

In another aspect of the invention, a needle used to place a suture in a material, such as a rotator cuff tendon and/or implant, may be engaged with a cannula, such as an arthroscopic cannula. Thus, the needle may be operated to place the suture by manipulating the cannula. The needle and cannula may have complementary locking members or otherwise arranged so that the needle may be selectively engaged with the cannula. Thus, the cannula may be usable as a standard arthroscopic cannula, and if needed, may be engaged with the needle. Thereafter, the needle and cannula may be used to place the suture in the selected tissue.

These and other aspects of the invention will be apparent from the following description.

FIG. 3 shows a schematic diagram of a surgical repair in accordance with aspects of the invention. As discussed above, although aspects of the invention are described with reference to a rotator cuff repair for ease of reference and understanding, aspects of the invention may be used in any surgical or other procedure, and may involve any suitable body portions, such as bone, muscle, other tissue or combinations thereof, vascular structures, digestive structures, medical implants or other devices, etc. Thus, aspects of the invention are in no way limited to the specific embodiments and examples described herein.

In this illustrative embodiment, a rotator cuff tendon 2 is secured by a suture 3 relative to a humerus 1. The suture 3 is placed in the tendon 2, for example, using a mattress stitch or other arrangement, and is passed through a passageway 5 formed through the humerus 1. In this embodiment, the passageway 5 is formed by first and second intersecting holes. A first hole 51 is formed vertically as shown in FIG. 3 from a first opening at or near a margin between the articulating surface 11 and the greater tuberosity 12 of the humerus 1. The second hole 52 is formed horizontally as shown in FIG. 3 from a lateral position on the humerus 1. The suture 3 is secured at the second opening of the second hole using a suture fixation device 4 that is positioned adjacent the second opening. Although in this embodiment the first and second holes 51 and 52 are arranged at approximately right angles, the first and second holes may be arranged at any suitable angle and may be colinear (i.e., at a 180 degree angle relative to each other).

A wire, other material or the suture 3 may be manipulated in the passageway 5 so as to cut through or crush the relatively soft cancellous bone of the humerus in the passageway 5 so that the suture follows a relatively straight path between the first and second openings into the first and second holes 51 and 52. The relatively straight pathway may be formed by a "flossing" operation, such as by using a wire that is passed through the passageway 5 and is manipulated, e.g., tensioned and reciprocally drawn between the first and second openings, so as to cut through or crush the cancellous bone, thereby forming a relatively straight path for the suture 3.

When deciding where to locate the first hole 51 for the passageway 5, a surgeon often will wish to first determine the final position for the tissue relative to the bone. To do so, the surgeon may wish to place a suture in the tendon 2 and tension the suture 3 (and thus the tendon 2) so that a desired position for the first hole 51 may be determined, e.g., based on the position of the tendon 2 relative to the bone when under tension.

In various aspects of the invention, a suture may be placed in the tendon or other tissue 2 using any suitable technique, such as a standard suturing needle and forceps, specialized suturing devices, and so on. However, in one aspect of the invention, use of a needle having a hook-shaped or curved end portion may be preferred. FIGS. 4-6 show an embodiment of a needle 6 having a hook-shaped tissue engaging portion 61 at a distal end in accordance with the invention. In the illustrated embodiment, the tissue engaging portion 61 of the needle 6 has a semi-circular shape and is arranged at an angle, such as 90 degrees to a longitudinal axis of a straight portion 62 of the needle 6. The needle 6 may be formed as a hollow tube so that the suture 3 may pass through the needle 6. Suture may be loaded in the hollow portion of the needle 6 before the surgical procedure is begun, e.g., at the time of manufacture of the needle, or at any suitable time, such as during the surgical procedure. In some cases, the suture may be fed into the hollow portion of the needle 6 before the tissue engaging portion 61 is formed, e.g., by bending a tube to form a curved end shape.

The arrangement of the needle 6 may allow placement of a mattress stitch in the tissue 2 by rotating the needle as shown in FIGS. 4-6 so that a tip of the tissue engaging portion 61 passes through a top side of the tissue 2 and exits from a bottom side of the tissue 2 as shown in FIG. 5, and then passes upwardly through the tissue 2 to reemerge at a top side of the tissue 2 as shown in FIG. 6. At this point, the suture 3 extending from the tip of the tissue engaging portion 61 may be grasped, such as by forceps or other gripping device, and the needle 6 may be rotated in reverse so as to again position the needle 6 as shown in FIG. 4, thereby leaving the suture 3 positioned in the tissue 2 to form a mattress stitch. During the passage of the suture, the tissue or other material may be held in place, or may be manipulated, by a grasper or other device inserted into the lumen of the cannula. The tissue or other material may also be held in place, or manipulated, by another device, such as a grasper or clamp positioned external to the cannula.

The tissue engaging portion 61 of the needle 6 may have any suitable shape and may be arranged in a plane that is transverse at any angle to an axis of rotation of the tissue engaging portion 61 when placing a suture in tissue. That is, although in the illustrated embodiment the tissue engaging portion 61 has a semi-circular form that lies in a plane at 90 degrees to the rotation axis of the tissue engaging portion 61 when placing a suture, the tissue engaging portion 61 need not have a semi-circular form and may lie at any desired angle to the rotation axis. For example, the tissue engaging portion 61 may be arranged so as to place an inclined mattress stitch in a tissue 2. Further, the needle 6 need not be used only to form a mattress stitch, but rather may be used to form any other suitable stitch type. Also, it is not necessary that the tissue engaging portion 61 of the needle 6 lie in a single plane. Instead, the tissue engaging portion 61 may not lie in a single plane, e.g., may have a corkscrew-type or partially helical configuration.

In one aspect of the invention, all or portions of a tissue repair procedure may be performed arthroscopically. In this case, and as is known in the art, one or more cannulas may be provided in one or more portals formed in the patient so as to provide access to the operative site. In one aspect of the invention, a needle used to place a suture in a tissue, such as the needle 6 shown in FIG. 4, may be used in an arthroscopic procedure. For example, the needle 6 may be secured to a cannula so that the needle may be operated by manipulation of the cannula.

FIG. 7 shows an illustrative embodiment of a needle 6 that is secured to a cannula 7. The cannula 7 may have any suitable features found in cannulas used for closed or minimally-invasive surgical techniques, such as one or more valves to resist fluid flow through the cannula 7, an opening through which to introduce a fluid pressure or vacuum, spiral threads or other features on the cannula to aid in placement of the cannula in a portal and/or to help prevent inadvertent removal of the cannula from the portal, and so on. The cannula 7 may be arranged for any type of procedure, such as arthroscopic procedures.

The needle 6 may be secured to the cannula 7 in any suitable way. For example, the needle 6 may be molded into the body of the cannula 7, inserted into the wall of the cannula, may be secured by adhesive, welding, clamps, fasteners, interlocking channels, open channels, or any other suitable device. A proximal end of the needle 6 may terminate at any suitable point, such as midway between a proximal end 71 and a distal end 72 of the cannula 7 as shown, or, more preferably at a position proximal to the proximal end 71. By having the proximal end of the needle 6 positioned proximally of the cannula 7, a user may be better able to access the suture 3 entering the proximal end of the needle 6. The needle 6 may also be axially movable relative to the cannula, e.g., so that the tissue engaging portion 61 may be moved axially so as to extend away from or toward the distal end 72 of the cannula 7. In addition, although the needle 6 is shown as positioned on an outer surface of the cannula 7, the needle 6, or at least a portion thereof, may be molded into the cannula 7, positioned within the cannula lumen, positioned within the cannula wall, may be arranged within a groove on the outer surface of the cannula, and so on. Although the needle 6 is shown as arranged in an approximately straight fashion along the length of the cannula 7, the needle 6 may be bent, curved or arranged in any suitable way, such as following a spiral path around an outer surface of the cannula 7.

In one illustrative embodiment, a semicircular-shaped tissue engaging portion 61 of the needle 6 may be arranged relative to the cannula 7 so that a centerpoint of the semicircle lies on a central longitudinal axis 73 of the cannula lumen. Thus, when the cannula 7 is rotated about the central longitudinal axis 73, the tissue engaging portion 61 may travel in a circular path about the axis 73. However, it should be understood that the tissue engaging portion 61 may be arranged in any suitable way relative to the axis 73. Further, a plane in which the tissue engaging portion 61 lies (if present) may be arranged at any angle transverse to the axis 73, and thus need not be arranged at an angle of 90 degrees to the axis 73, as shown in FIG. 7.

In one aspect of the invention, the needle 6 may be removeably engaged with the cannula 7 so that the needle 6 can be selectively engaged or disengaged with the cannula 7. For example, a cannula 7 may be positioned in a portal in use during a surgical procedure without an attached needle 6. At some point during the procedure, the surgeon may wish to attach a needle 6 to the cannula 7 and manipulate the cannula 7 so as to use the needle 6 to place a suture in a tissue. The needle 6 may be secured to the cannula while the cannula remains in place in the portal (e.g., by inserting the needle 6 into the cannula lumen), or the cannula may be removed from the portal, the needle attached, and the cannula and attached needle inserted into the portal.

Figure 8:
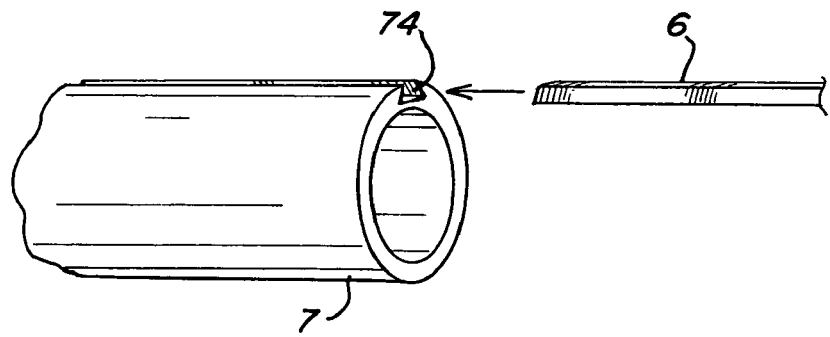
FIG. 8 shows an illustrative arrangement for engaging a needle with a cannula in one embodiment.

FIG. 8 shows one illustrative embodiment in which a needle 6 may be removably secured to a cannula 7. In this embodiment, the cannula 7 includes a dovetail-shaped groove 74 into which a correspondingly shaped portion of the needle 6 is inserted. The complementary locking arrangement used by the cannula 7 and the needle 6 need not necessarily be dovetail-shaped as shown in FIG. 8, but rather may have any suitable arrangement. For example, the cannula 7 may have an oval-shaped channel that receives an oval-shaped portion of the needle 6. Thus, the needle 6 may be selectively secured to the cannula 7 so that rotation or other manipulation of the cannula 7 can cause the needle to be manipulated so as to place a suture in a tissue. The complementary locking arrangement between the needle 6 and the cannula 7 may also allow for axial movement of the needle 6 relative to the cannula 7, e.g., so the tissue engaging portion 61 can be moved relative to the distal end 72 of the cannula 7.

Figure 9:
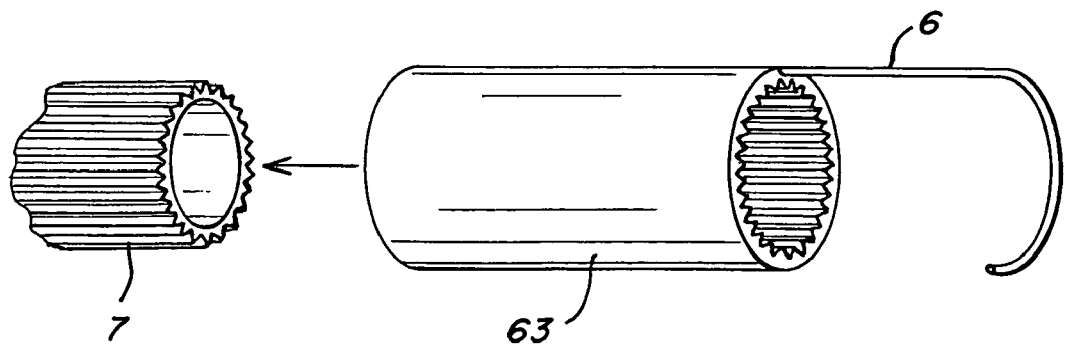
FIG. 9 shows an illustrative arrangement for engaging a sleeve and needle assembly with a cannula in accordance with another embodiment.

FIG. 9 shows an alternative embodiment in which a needle 6 is fixed to a sleeve member 63 that has one or more complementary locking features that mesh with or otherwise engage with complementary features on the cannula 7. In this embodiment, the complementary locking features have a tooth-like or gear-like form, but the complementary locking features may be arranged in any suitable way. Accordingly, in this embodiment, the needle 6 may be secured to the cannula 7 by sliding the sleeve 63 over the distal end 72 of the cannula 7. It will be understood that rather than having a sleeve 63 that fits over the cannula 7, the sleeve 63 may fit within the internal lumen of the cannula 7, or within a slot in the cannula 7, if desired.

Once a suture is placed in the tissue, such as a rotator cuff tendon, the tissue may be tensioned to determine a location for the opening of the first hole 51 to be formed in the bone. When performing a rotator cuff repair, a first hole 51 of the passageway 5 may be formed vertically from a superolateral position so that the first hole 51 is generally aligned along the length of the humerus 1 and extends into the bone from an opening formed at the margin between the articulating surface 11 and the greater tuberosity 12. This first hole 51 may be formed using a perforator, such as a drill, awl, punch or other suitable device. As with other procedures performed, the first hole 51 may be formed using an arthroscopic portal at a superolateral position, or may be formed in an open surgical procedure.

Figure 10:
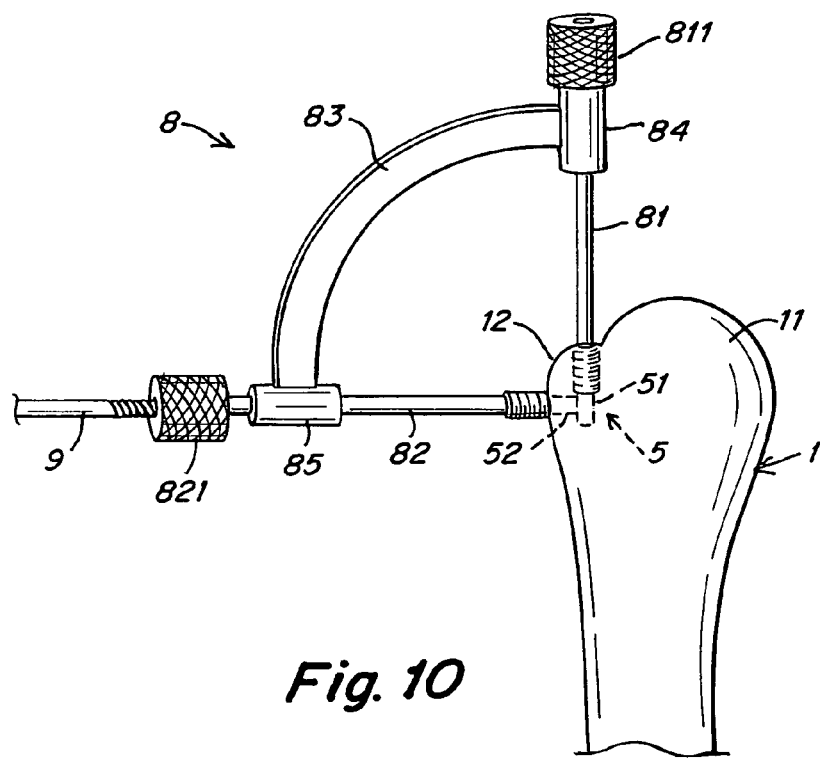
FIG. 10 shows a guide apparatus used in forming a passageway in accordance with the invention.

In accordance with an aspect of the invention, a guide apparatus may be used to form the first and/or second holes of the passageway (e.g., used to locate a starting point or opening for the first and second holes, used to orient a bone perforator when making the holes, or used alone to form the first and/or second holes), or may be used to help feed a suture or suture-like material through the passageway. For example, a first guide member 81 may be secured relative to the first hole 51, as shown in FIG. 10. The first guide member 81 may be part of a guide apparatus 8 used to guide the formation of holes used to form a passageway in bone and/or to pass a suture or other material through the passageway. In the illustrated embodiment, the first hole 51 has been formed in a vertical direction along the length of the humerus 1, e.g., by drilling the hole in a freehand manner. (Alternately, the first hole 51 may be formed by forcing the first guide member 81 into the bone as with an awl or similar instrument.) The first guide member 81 may include a feature to help secure the first guide member 81 relative to the first hole 51, such as a threaded distal end that allows the first guide member 81 to be screwed into the bone to a desired depth in the first hole 51. It should be understood, however, that the distal end of the first guide member 81 need not be threaded, but instead may unthreaded and inserted into the first hole 51. Alternately, the distal end of the first guide member 81 may be positioned outside of, but adjacent to, the first hole 51 so that a lumen in the first guide member 81 aligns with the first hole 51. The first hole 51 may be formed so as to be deeper than thought to be needed, e.g., 0.5 cm deeper than a hole depth believed to be required. This overdrilling of the first hole 51 may allow for more flexibility in positioning the first guide member 81 to a desired depth in the bone.

The first guide member 81 may be arranged with respect to a reference structure 83 used to position first and second guide members 81 and 82 relative to each other with respect to the passageway 5, as is discussed in more detail below. In this illustrative embodiment, the reference structure 83 is arranged so that the first and second guide members 81 and 82 are positioned at a 90 degree angle relative to each other when engaged with the reference structure 83. However, the reference structure 83 may be arranged in any suitable way so as to orient the first and second guide members 81 and 82 at any desired angle relative to each other, including arranging the first and second guide members 81 and 82 in a co-linear fashion. Further, the reference structure 83 may be made so as to be adjustable, thereby allowing the orientation of the first and second guide members 81 and 82 to be changed. For example, the arc-shaped connecting portion of the reference structure 83 may be made so as to be adjustable in length, e.g., having one arc-shaped portion sliding relative to another arc-shaped portion to allow adjustment of the length of the connecting portion. Alternately, or in addition, engagement portions 84 and 85 of the reference structure 83 that engage with the first and second guide members 81 and 82 may be adjustable in orientation relative to the arc-shaped connecting portion. In short, the reference structure 83 may be arranged in any suitable way so as to allow adjustment in the orientation of the guide members 81 and 82.

In this illustrative embodiment, the engagement portions 84 and 85 include sleeves that receive at least a portion of the guide members 81 and 82, e.g., the guide members 81 and 82 may be received in bores in the sleeves. The sleeves may be arranged so that the guide members 81 and 82 are movable linearly along their longitudinal axes and rotationally about their longitudinal axes relative to the engagement portions 84 and 85, but otherwise may be relatively restricted in their range of movement. When a stop on the first guide member 81, such as a knob 811 on the proximal end of the guide member 81, contacts an engagement surface on the reference structure, such as a portion of the engagement portion 84, the second guide member 82 may be positioned by the reference structure 83 so that its longitudinal axis passes a point adjacent the extreme distal end of the first guide member 81. Thus, the second guide member 82 may be used to guide the use of a perforator 9 (such as a drill, punch, awl or other bone perforating device) so that the perforator 9 forms a second hole 52 that intersects with the first hole 51 at a location adjacent the distal end of the first guide member 81. As discussed above, the guide member 82 may guide the movement of the perforator 9, e.g., guide the movement of a drill or punch inserted into a lumen of the guide member 82 as shown, or may guide a starting location for forming the second hole, e.g., be used to mark or otherwise determine a starting location for the perforator 9, but otherwise not interact with the perforator 9. By adjusting the depth of the first guide member 81 in the first hole 51, the location where the second hole 52 is formed can be adjusted in position (e.g., in a vertical direction as shown in the figures). For example, by screwing the first guide member 81 into or out of the first hole 51, a surgeon may select a location where the second hole 52 is to be formed in the bone.

In another embodiment, the engagement portion 85 may itself function as a perforator guide with the second guide member 82 being withdrawn from the engagement portion 85. Although in this illustrative embodiment the engagement portions 84 and 85 are shown as relatively short cylindrical sleeves, the engagement portions 84 and 85 may be arranged in any suitable way, e.g., may be elongated so as to more closely approach the humerus 1 and provide improved guidance for a perforator 9 and/or the first and second guide members 81 and 82. Further, the first guide member 81 may be arranged so that is rotationally movable about its longitudinal axis relative to the reference structure 83, but is otherwise held by the engagement portion 84 so that the first guide member 81 is not movable axially. This may aid is appropriately positioning the first guide member 81 and reference structure 83 when forming the second hole 52.

Figure 11:
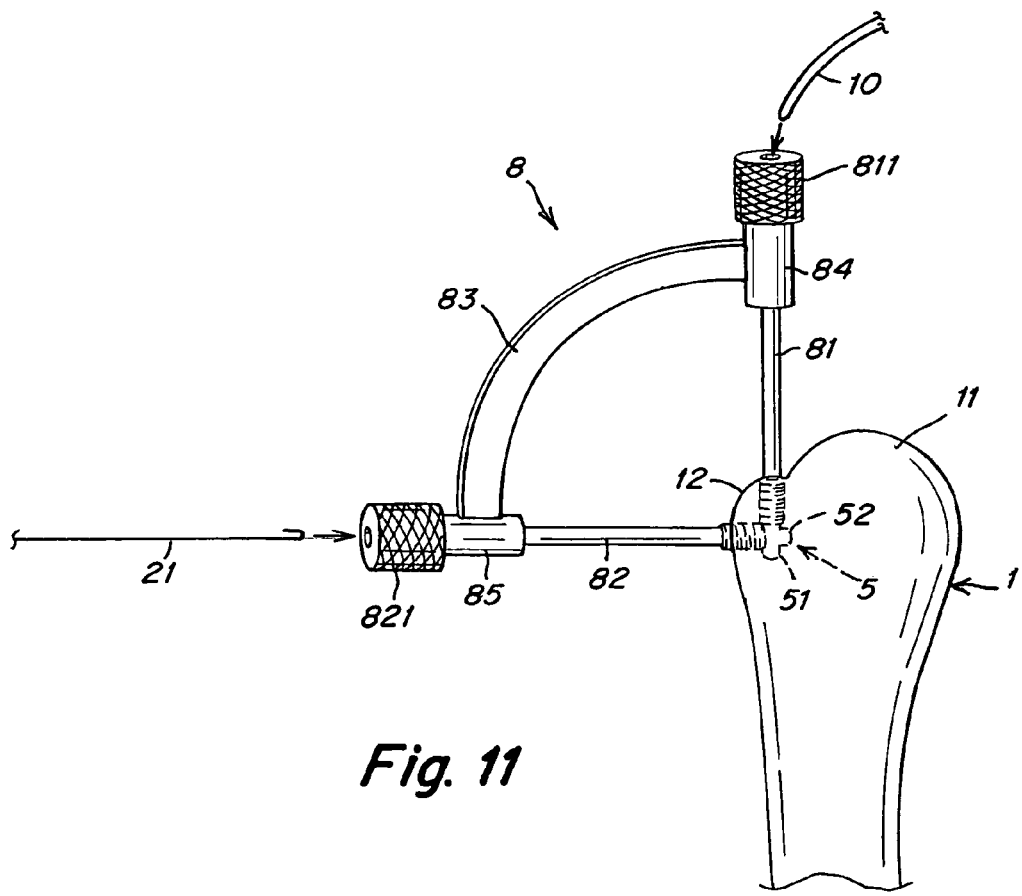
FIG. 11 shows the use of a guide apparatus for passing a suture or other element through a transosseous passageway in accordance with the invention.

Upon formation of the second hole 52, the second guide member 82 may be screwed into the second hole 52 until a stop on the second guide member 82, such as a knob 821 at a proximal end of the guide member 82, contacts an engagement surface on the engagement portion 85, such as a portion of the sleeve. In this configuration shown in FIG. 11 (stops on the first and second guide members 81 and 82 engaged with respective engagement surfaces on the reference structure 83), the extreme distal ends of the first and second guide members 81 and 82 may be adjacent to each other in the passageway 5 formed by the first and second holes 51 and 52. Accordingly, a surgeon may be assured that if the first and second guide members 81 and 82 are positioned within the bone and stops on the guide members 81 and 82 are respectively in contact with appropriate engagement surfaces on the guide apparatus 8, the extreme distal ends of the guide members 81 and 82 will be positioned adjacent each other. Thus, the surgeon may be assured that a wire 10 or other element may be fed into one of the guide members and retrieved from the other of the guide members, e.g., using a retriever 21 having a hook at a distal end. Such an arrangement may be advantageous when using the guide apparatus 8 in an arthroscopic procedure where the operative site may not be easily visualized.

Although in the above embodiment, stops on the first and second guide members 81 and 82 contact corresponding engagement surfaces on the engagement portions 84 and 85, the guide members 81 and 82 may be positioned relative to the reference structure 83 in any suitable way. For example, the guide members 81 and 82 may have indicator marks on them that may be aligned with a portion of the engagement portions 84 and 85, respectively. The alignment of certain indicator marks on the guide members 81 and 82 may be used to indicate, for example, that the distal ends of the guide members 81 and 82 are adjacent each other. Those of skill in the art will understand that the position of the guide members 81 and 82 relative to the reference structure 83 and relative to each other may be determined in other ways. For example, the first and second guide members 81 and 82 need not necessarily be positioned so that their distal ends are adjacent in the passageway to assist in feeding a suture from one guide member to the other. Instead, the first and second guide members 81 and 82 may be made to suitably communicate with the passageway in any way so as to facilitate feeding of the suture.

In this illustrative embodiment, the first guide member 81 is shown as having a smaller diameter (at least at the distal end) than the second guide member 82. This may allow the guide apparatus 8 to be used with an arrangement where the first hole 51 is smaller than the second hole 52. A relatively small first hole 51 may allow for more rapid healing and/or provide additional space for other holes in the margin, if needed. However, it should be understood that the guide apparatus 8 and/or the holes that form the passageway 5 may be made in any suitable way, e.g., the first and second holes 51 and 52 may have the same diameter or the first hole 51 may have a larger diameter than the second hole 52.

The guide apparatus 8 may also include additional guide members if desired, e.g., to provide for the formation of a third hole that is formed in the margin and is approximately parallel to the first hole 51, but also intersects with the second hole 52. Similarly, the guide apparatus 8 may include two pairs of guide members like that in the illustrative embodiment that are arranged to form side-by-side passageways 5 in the bone or other body portion.

Although in this illustrative embodiment, the guide apparatus 8 is used to guide the formation of the second hole 52, the guide apparatus 8 need not necessarily be used to guide the formation of the second hole 52. That is, the guide apparatus 8 may be used only to help feed the wire 10, suture or other material through a passageway that is pre-formed in the bone or other body portion. In addition, the first and second guide members 81 and 82 may be arranged so that the members 81 and 82 can be secured in a body portion without requiring holes to be predrilled or otherwise formed. Thus, in one embodiment, the first and second guide members 81 and 82 may be arranged like an awl or other device capable of forming a hole in a body portion, e.g., capable of being forced into bone, forming the passageway 5 by their entry and/or providing a means to help feed a wire, suture or other material through the passageway 5.

Figure 12:
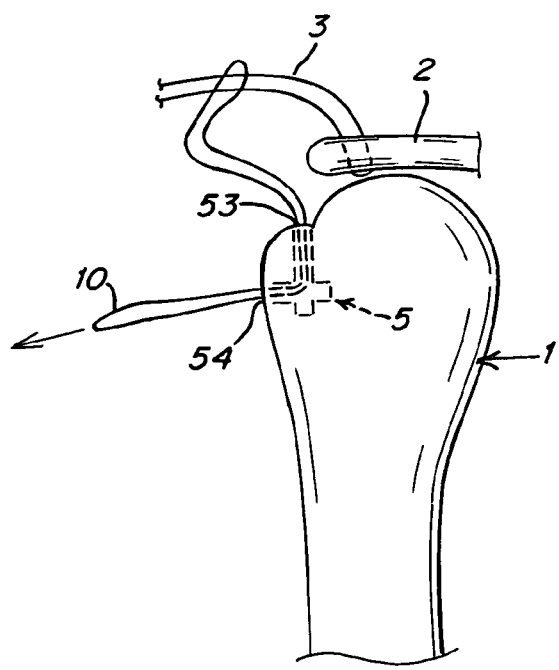
FIG. 12 shows a technique for passing a suture placed in a tissue through a passageway.

Once the wire 10, suture or other material has been passed through the passageway 5, as shown in FIG. 12, the wire 10 may be used to pull the suture 3 through the passageway 5. Prior to being used to pull the suture 3 through the passageway 5, the wire 10 or other material may be used to create a relatively straight pathway for the suture 3 once the suture 3 is tensioned and fixed in place. For example, the wire 10 may be tensioned between the first and second openings 53 and 54 of the first and second holes 51 and 52 or otherwise manipulated so as to cut or crush the body portion, e.g., bone, between the first and second openings 53 and 54. Such manipulation of the wire 10 may perform a kind of "flossing" effect in the bone, allowing the suture 3 to follow a more straight pathway through the passageway 5, reducing the length of suture 3 needed between the rotator cuff 2 and a point of fixation of the suture 3, e.g., near the second opening 54. The wire 10 may have barbs or other saw-like features to aid in cutting bone and forming the pathway. Of course, the more straight pathway could be formed by manipulating the suture 3 itself, e.g., by tensioning the suture 3 when securing the tendon or other material. Reducing the length of suture 3 in the passageway 5 may improve the suture's ability to maintain appropriate tension on the rotator cuff 2, e.g., by reducing the amount of stretch of the suture when under tension.

Figure 13:
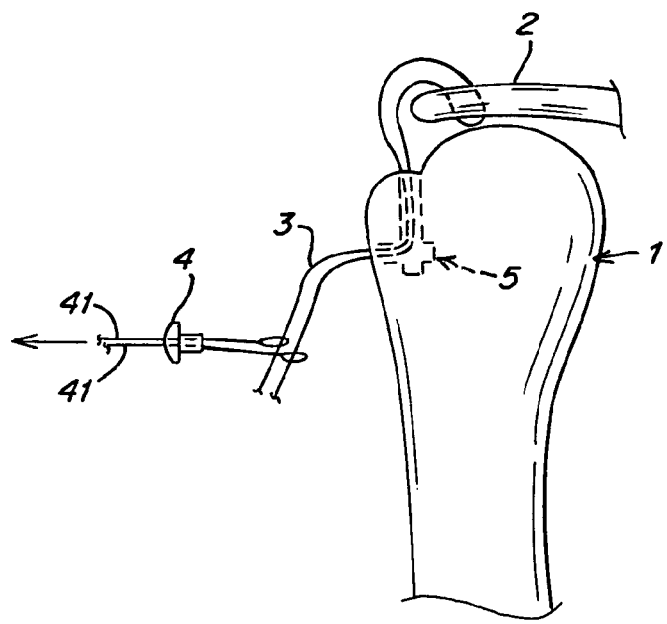
FIG. 13 shows the engagement of a suture with a suture fixation device in accordance with the invention.

After the suture 3 has been passed through the passageway 5, the suture 3 may be engaged with a suture fixation device 4 as shown in FIG. 13. Although use of a suture fixation device is not required, the suture fixation device 4 may improve an ability to securely fixate the suture 3 (and the tissue 2) relative to the bone. The suture fixation device 4 may be arranged in any suitable way, but in this illustrative embodiment has an arrangement similar to a button. For example, the suture fixation device 4 may have two through holes formed in a disk-shaped member through which leading ends of the suture 3 are passed. The suture ends 3 may be passed through respective holes in the suture fixation device 4 using one or more feed members 41. The feed members 41 may have an elongated shape that is passed through a respective hole in the suture fixation device 4. A loop at one end of the feed member 41 may receive an end of the suture 3 and thereafter the feed member 41 may be pulled through a respective hole in the suture fixation device 4 so as to pull the suture 3 through the hole. The feed member 41 may include one or more flat plates or strips, e.g., made of metal or plastic, with a hole or recess to accept suture. The flat configuration may allow for easy passage through the restriction portion of the device. Although some resistance may be encountered when feeding the portion of the feed member 41 that engages the suture through the restriction, permanent damage or other compromise of the resistive properties of the restriction may be avoided. Of course, it should be understood that the suture 3 may be fed through the suture fixation device 4 in any other suitable way. When performing this technique arthroscopically, the suture 3 may be fed through the suture fixation device 4 either inside or outside of the body cavity.

Figure 14:
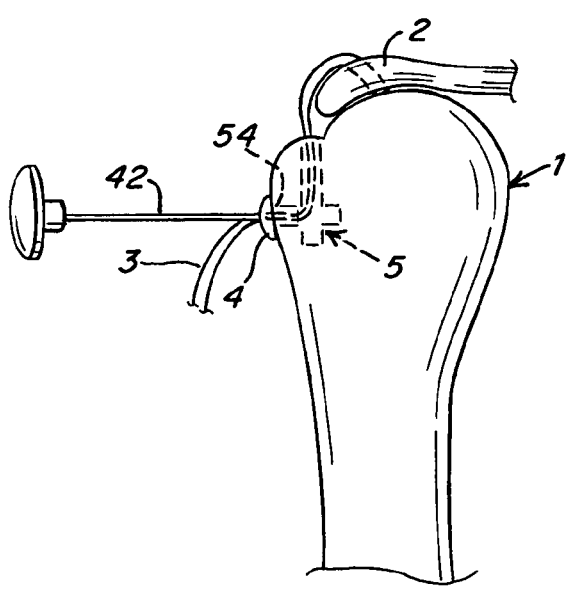
FIG. 14 shows the placement of a suture fixation device relative to the bone in accordance with the invention.
Figure 15:
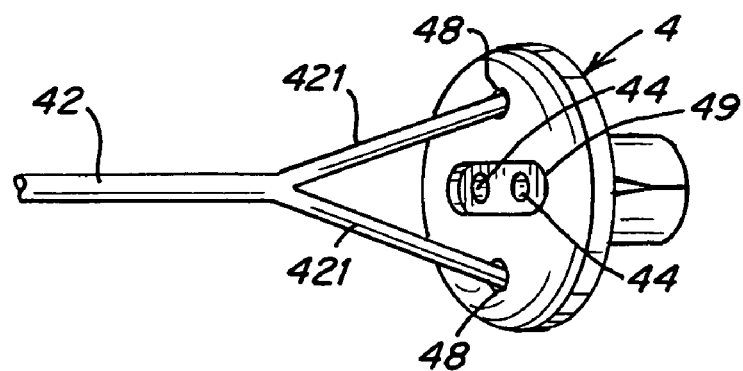
FIG. 15 shows a suture fixation device engagement tool in engagement with a suture fixation device in accordance with the invention.
Figure 16A:
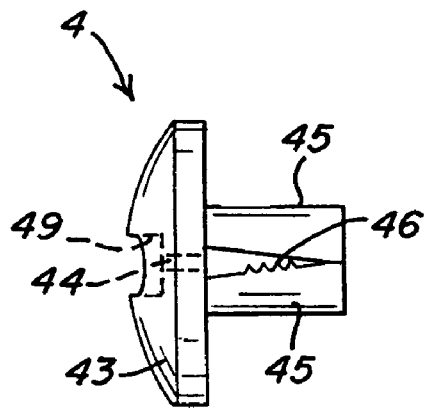
FIGS. 16A-B and 17A-B show side and rear views, respectively, of illustrative embodiments of suture fixation devices in accordance with the invention.
Figure 16B:
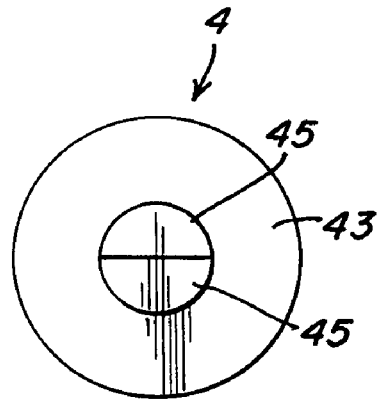
Figure 17A:
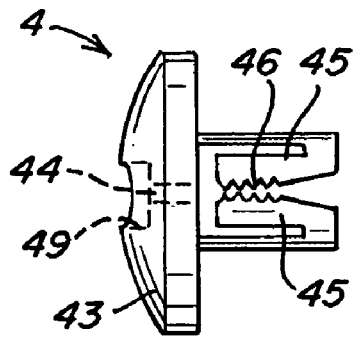
Figure 17B:
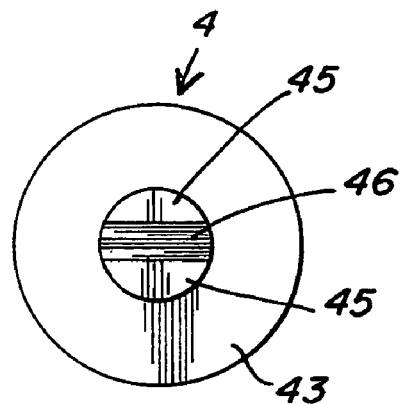

As shown in FIG. 14, after the suture 3 is engaged with the suture fixation device 4, the suture fixation device 4 may be positioned relative to the second opening 54 of the passageway 5 using an applier 42 which removably engages with the suture fixation device 4 and may be selectively disengaged from the suture fixation device when the suture fixation device 4 is positioned as desired. As shown in FIG. 15, the applier 42 may have a pair of tines 421 that engage with recesses or other features on the suture fixation device 4 so as to removably engage with the suture fixation device 4. The tines 421 may be resilient so that the tines are squeezed together when engaged with the suture fixation device 4. Thus, an elastic force biasing the tine ends apart may help maintain engagement of the tines with the grooves 48 in the suture fixation device 4. Alternately, the tine ends may be force-fit into grooves 48 in the suture fixation device so that engagement is maintained based on friction. Of course, it will be understood that the applier 42 may engage with the suture fixation device 4 in any other suitable way, such as a screw-in or snap configurations.

With the suture fixation device 4 in place relative to the second opening 54, the suture 3 may be tensioned so as to appropriately position the rotator cuff 2 relative to the humerus 1. At this point, the suture 3 may be fixed relative to the suture fixation device 4, such as by tying a knot with the suture ends. Thus, the suture fixation device 4 may provide not only a structure to support the suture knot, but also may spread the force of the suture 3 to portions of the relatively hard cortical bone surrounding or otherwise adjacent to the second opening 54. By having the suture fixation device 4 engage with this cortical bone, the suture fixation device 4 may provide a relatively stable and secure fixation point for the suture 3. The suture fixation device 4 may also incorporate a mechanism for knotless fixation of the suture, such as an interference pin, a locking passageway, a locking cap, etc.

Although in the illustrative embodiment described above both ends of the suture 3 are passed through the passageway 5 and secured at or near the second opening 54 of the passageway 5, the suture 3 may be secured in other ways, such as by passing one end of the suture 3 through the passageway 5 and passing another end of the suture 3 around the outside of the bone (e.g., over a portion of the greater tuberosity) where it is secured to the other suture end. In another embodiment, two passageways 5 may be formed through the bone and one end of the suture 3 may be passed through one passageway and the other end of the suture 3 may be passed through the other passageway. The suture ends may then be secured to each other at or near respective second openings of the passageways 5 on the lateral side of the humerus 1. In yet another embodiment, two or more first holes 51 may be formed so as to intersect with one or more second holes 52. Suture 3 may be passed through the two or more first holes 51 and be secured at the second opening 54 of the one or more second holes 52. Such an arrangement may allow for the use of a single second hole 52 and suture fixation device 4 to secure the rotator cuff at two or more points on the humeral head using two or more sutures that pass through different first holes 51. Other suture fixation techniques may be used as desired.

FIGS. 16A-B and 17A-B show illustrative embodiments of suture fixation devices 4 in accordance with the invention. In these embodiments, the suture fixation device 4 includes a restriction in a pathway through the suture fixation device 4 so that suture or other material passing through the suture fixation device is relatively freely moved in one direction through the pathway, but movement of the suture or other material in the other direction in the pathway is resisted. For example, movement of a suture though the suture fixation devices shown in FIGS. 16A and 17A in a direction to the left in the side view of the suture fixation devices 4 may be freely allowed, while movement of the suture toward the right may be resisted. This may aid in tensioning the suture 3 because the suture 3 may be pulled from the second hole 52 through the suture fixation device 4 until the rotator cuff or other tissue is appropriately positioned. Thereafter, tension on the suture may be temporarily released, e.g., in preparation for forming a knot, but movement of the suture back through the suture fixation device 4 may be resisted so that the rotator cuff or other tissue is maintained in place until the suture knot is tied or otherwise is secured.

In the FIG. 16 embodiment, the suture fixation device includes an outer end having a flange portion 43 that is sized and arranged to contact the cortical bone adjacent the opening in the passageway at which the suture fixation device 4 is positioned, e.g., the second opening 54. One or more pathways 44 may be formed through the suture fixation device 4, such as by a hole or holes formed through the flange 43 (see also FIG. 15). Instead of having multiple holes, the pathway 44 may include a single slot arranged to receive one or more sutures. A recess 49 may be provided in the flange portion 43 to receive one or more knots, if formed with the suture(s) in the pathway 44. A pair of duck bill members 45 at an inner end of the suture fixation device 4 may extend rearwardly from the flange 43 and may be arranged as to be positionable in the second hole 54. The duck bill members 45 may be separated from each other by a groove that extends across the inner end of the suture fixation device 4 and be resiliently biased toward each other so as to resist the passage of suture or other material through the pathway 44. One or both of the duck bill structures 45 may include serrations 46 or other features that may aid in engaging a suture or other material. In the FIG. 16 embodiment, the groove separating the duck bill structures 45 extends to the flange portion 43 so that the structures 45 are pivotable at a point near the flange portion 43.

The FIG. 17 embodiment similarly includes a flange 43 and one or more pathways 44. Duck bill structures 45 are also provided. However, in this embodiment rather than being hinged at a point near respective connection points with the flange 43, the duck bill portions 45 are hinged at a point positioned away from the flange 43. Providing the effective hinge points for the duck bill structures 45 in this manner may provide improved engagement of the duck bill structures 45 with a suture or other material when the suture is urged to move from the outer end toward the inner end through the pathway 44. That is, if the suture is pulled to move toward the inner end, serrations 46 or other features will engage with the suture and increased force on the suture will cause an increased force urging the duck bill structures 45 to move toward each other and further squeeze the suture. The duck bill structures in the FIGS. 16 and 17 embodiments or other suitable suture engagement arrangements (such as interference pins, locking caps, locking internal hubs, etc.) may provide a knotless fixation for the suture. Alternatively, the structures may resist movement of the suture so as to aid the surgeon's ability to maintain tension on the suture while forming a knot.

Although this embodiment depicts the flange of the device resting on the outer cortical surface of the bone, the device may be positioned in a hole which has a counterbore, or countersink, in order to prevent any interference between the flange and other bone or tissues that may come in contact with the site either at rest or during movement. Even in the case where the device is positioned in a counterbore or countersink feature, the device may contact cortical bone. Alternately, the device may only contact the outer, cortical surface of the bone, and not extend into a hole in the bone.

Of course, it should be understood that suture fixation devices may be provided in any suitable form. For example, the duck bill portions 45 extending from the flange 43 in the FIGS. 16 and 17 embodiments may be sized to closely fit into a mating hole formed in bone. This close fit may help in maintaining the suture fixation devices 4 in a desired position in the bone. Alternately, the duck bill structures 45 may be formed so as to be tapered on their outer surfaces. Thus, when the suture fixation device 4 is inserted into a hole in the bone, the tapered surfaces of the duck bill structures 45 may contact the sides of the hole and urge the duck bill structures to move toward each other as the suture fixation device 4 is pressed into the hole. In another embodiment, a portion of the suture fixation device 4 that is inserted into a hole may be threaded or otherwise be arranged so as to engage the hole and help prevent the suture fixation device from falling from the hole, e.g., before the suture is secured in place. There are many variations of the mechanism form to retain the suture with respect to the device. Some of these forms may require a knot for final fixation. Other capturing mechanisms may provide sufficient locking of the suture such that a knot is not required. Theses are typically known as "knotless" devices.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for performing a surgical repair, comprising:

providing a first hole in a body portion;

positioning a first portion of a guide relative to the first hole, the first portion extending at least partially into the first hole;

forming a second hole transverse to the first hole using a second portion of the guide so that the second hole is aligned with the second portion of the guide and intersects with the first hole and forms a passageway with the first hole through the body portion;

using the first and second portions of the guide, while the first and second portions of the guide remain fixed in place relative to each other and relative to the first and second holes, to provide a suture through the passageway by providing the suture through a passage extending along a length of the first or second portion of the guide and into the passageway and retrieving the suture using the other of the first or second portion;

securing a repair suture to a material to be secured relative to the body portion;

positioning at least a portion of the repair suture in the passageway; and securing the material relative to the body portion using the repair suture.

2. The method of claim 1, further comprising:
providing at least one arthroscopic portal though tissue for access to at least one portion of the body portion; and
using the at least one arthroscopic portal to form the passageway.

3. The method of claim 1, wherein the step of positioning a first portion of a guide comprises:
placing a first guide member relative to the first hole;
positioning the first guide member relative to a reference structure; and
positioning a second guide member relative to the reference structure, wherein the second guide member is used to form the second hole.

4. The method of claim 3, wherein the step of forming the second hole comprises:
using the second guide member to define a starting point for the formation of the second hole or to guide the movement of a perforator.

5. The method of claim 3, wherein the first and second guide members each include a tube that is securable in the first and second holes, respectively.

6. The method of claim 5, further comprising:
positioning the first guide tube relative to the reference structure at a first position; and
positioning the second guide tube relative to the reference structure at a second position so that distal ends of the first and second guide tubes are adjacent each other in the body portion.

7. The method of claim 6, wherein the step of using the guide comprises:
positioning the suture in the first guide tube; and retrieving the suture from the second guide tube.

8. The method of claim 7, wherein the step of retrieving comprises:
inserting a suture retriever into the second guide tube;
engaging the suture in the first guide tube with a suture retriever; and
withdrawing the suture retriever and engaged suture from the second guide tube.

9. The method of claim 8, wherein the suture withdrawn from the second guide tube is a lead material, the method further comprising:
attaching the repair suture to the lead material; and
drawing the lead material through the passageway to feed the repair suture into the passageway.

10. The method of claim 1, wherein the step of positioning at least a portion of the repair suture comprises:
positioning two free ends of the repair suture in the passageway.

11. The method of claim 10, wherein the step of securing the material comprises:
using a suture fixation device to secure the repair suture relative to the passageway.

12. The method of claim 1, wherein the body portion is a bone and the material is a tissue to be secured relative to the bone.

13. The method of claim 1, wherein the step of securing a repair suture comprises:
manipulating a needle and repair suture attached to a cannula so as to secure the repair suture to the material.

14. The method of claim 13, wherein the needle has a hollow portion through which the repair suture passes, and the step of manipulating comprises rotating the cannula to move a needle end along an arc-shaped path to place the repair suture in the material.

15. The method of claim 14, further comprising:
grasping the repair suture near the needle end after moving the needle end along an arc-shaped path; and
moving the needle end in a reverse direction to disengage the needle from the material while leaving the repair suture engaged with the material.

16. The method of claim 13, wherein the step of manipulating the needle comprises:
placing the repair suture to form a mattress stitch in the material.

17. The method of claim 1, wherein the material is a rotator cuff, and the body portion is part of a humerus.

18. The method of claim 17, further comprising:
providing a superolateral arthroscopic portal;
providing a lateral arthroscopic portal; and
using the superolateral and lateral arthroscopic portals to form the passageway.

19. The method of claim 18, wherein the first hole is formed in a first direction into the humerus using the superolateral arthroscopic portal; and
the second hole is formed in a second direction into the humerus using the lateral arthroscopic portal so that the second hole intersects the first hole.

20. A method for forming a passageway in bone, comprising:
providing a first hole into bone of a humerus, the first hole extending into but not through the bone;
securing a first guide member relative to, and at least partially in, the first hole the first guide member including a first guide tube;
positioning the first guide member with respect to a reference structure at a first position;
positioning a second guide member with respect to the reference structure, the second guide member including a second guide tube, and positioning of the second guide member being independent of the first guide member;
drilling or punching a second hole in the humerus bone using the second guide member positioned with respect to the reference structure and using the second guide member to guide the orientation in which the second hole is formed, the second hole being formed so as to be aligned with the second guide member, and be transverse to and intersect the first hole and form a passageway though the humerus bone, the second hole extending into but not through the bone;
positioning the second guide member with respect to the reference structure at a second position such that distal ends of the first and second guide tubes are adjacent each other in the bone;
passing at least a portion of a suture through the passageway in the humerus bone by positioning at least a portion of the suture in the first or second guide tube and retrieving the suture from the other of the first or second guide tube; and securing a rotator cuff tendon to the humerus bone using the suture.

21. The method of claim 20, wherein the step of passing comprises:
inserting a suture retriever into the second guide tube;
engaging the suture in the first guide tube with the suture retriever; and
withdrawing the suture retriever and engaged suture from the second guide tube.

22. The method of claim 21, wherein the suture withdrawn from the second guide tube is a lead suture, the method further comprising:
securing a repair suture to a tissue to be secured to the bone;
attaching the repair suture to the lead suture;
drawing the lead suture through the passageway to feed the repair suture into the passageway; and
securing the repair suture relative to the passageway.

23. The method of claim 20, further comprising:
securing a suture to the rotator cuff tendon;
passing the suture though the passageway; and
securing the suture relative to the passageway so as to secure the rotator cuff tendon relative to the bone.

24. The method of claim 20, wherein the step of securing the first guide member comprises screwing a distal end of the first guide member into the first hole, the method further comprising:
screwing a distal end of the second guide member into the second hole so that the distal ends of the first and second guide members are adjacent.

25. The method of claim 24, wherein the step of positioning the first guide member comprises abutting a portion of the first guide member against an engagement surface on the reference structure; and
the step of positioning the second guide member with respect to the reference structure at the second position comprises positioning the second guide member relative to the first guide member by abutting a portion of the second guide member against an engagement surface on the reference structure.

26. The method of claim 20, further comprising:
manipulating a suture-like material in the passageway to form a straightened pathway through the bone.

* * * * *

UNITED STATES PATENT AND TRADEMARK OFFICE
CERTIFICATE OF CORRECTION

| | | |
|---|---|---|
| PATENT NO. | : 7,569,059 B2 | Page 1 of 1 |
| APPLICATION NO. | : 11/110540 | |
| DATED | : August 4, 2009 | |
| INVENTOR(S) | : Daniel Cerundolo | |

It is certified that error appears in the above-identified patent and that said Letters Patent is hereby corrected as shown below:

At column 15, claim 2, line 16, "though" should read -- through --

At column 16, claim 20, line 56, "though" should read -- through --

At column 17, claim 23, line 20, "though" should read -- through --

Signed and Sealed this

Twenty-second Day of September, 2009

David J. Kappos
*Director of the United States Patent and Trademark Office*